(12) United States Patent
Stewart et al.

(10) Patent No.: US 9,657,360 B2
(45) Date of Patent: May 23, 2017

(54) DETECTION OF VIRAL INFECTION

(75) Inventors: Cameron Stewart, East Geelong (AU); Andrew Bean, East Geelong (AU)

(73) Assignee: COMMONWEALTH SCIENTIFIC AND INDUSTRIAL RESEARCH ORGANISATION, Campbell (AU)

(*) Notice: Subject to any disclaimer, the term of this patent is extended or adjusted under 35 U.S.C. 154(b) by 0 days.

(21) Appl. No.: 14/344,886

(22) PCT Filed: Sep. 13, 2012

(86) PCT No.: PCT/AU2012/001090
§ 371 (c)(1),
(2), (4) Date: Dec. 5, 2014

(87) PCT Pub. No.: WO2013/036993
PCT Pub. Date: Mar. 21, 2013

(65) Prior Publication Data
US 2015/0105277 A1  Apr. 16, 2015

Related U.S. Application Data

(60) Provisional application No. 61/533,978, filed on Sep. 13, 2011.

(51) Int. Cl.
| | | |
|---|---|---|
| C07H 21/02 | (2006.01) | |
| C07H 21/04 | (2006.01) | |
| C12Q 1/70 | (2006.01) | |
| C12Q 1/68 | (2006.01) | |

(52) U.S. Cl.
CPC ........... *C12Q 1/701* (2013.01); *C12Q 1/6883* (2013.01); *C12Q 2600/158* (2013.01); *C12Q 2600/16* (2013.01); *C12Q 2600/178* (2013.01)

(58) Field of Classification Search
CPC .............................. C12N 15/113; A61K 23/10
See application file for complete search history.

(56) References Cited

U.S. PATENT DOCUMENTS

| | | |
|---|---|---|
| 2004/0072228 A1 | 4/2004 | Glynne et al. |
| 2006/0258752 A1 | 11/2006 | Vander Jagt et al. |
| 2007/0031410 A1 | 2/2007 | Harton et al. |
| 2007/0213292 A1 | 9/2007 | Stoffel et al. |
| 2007/0292878 A1 | 12/2007 | Raymond et al. |
| 2010/0292099 A1* | 11/2010 | Dreyfus et al. ...... C12N 15/113 506/10 |

FOREIGN PATENT DOCUMENTS

| | | |
|---|---|---|
| WO | WO 2008/036765 | 3/2008 |
| WO | WO 2009/100955 | 8/2009 |
| WO | WO 2011/057487 | 5/2011 |

OTHER PUBLICATIONS

Supplementary European Search Report and Search Opinion, issued Mar. 18, 2015 in connection with European Patent Application No. 12831844.1.
Communication Pursuant to Rules 70(2) and 70a(2) EPC issued Apr. 7, 2015 in connection with European Patent Application No. 12831844.1.
Chinese Patent Application No. CN 101 974 531, Kunmin Inst. Zoology CAS, Feb. 16, 2011, including English language translation.
Chinese Patent Application No. CN 102 021 169, Univ. Nanjing, Apr. 20, 2011, including English language translation.
Cameron et al (2008) "Epstein-Barr Virus Latent membrane Protein 1 Induces Cellular MicroRNA miR-146-a, A Modulator of Lymphocyte Signaling Pathways", Journal of Virology 82(4): 1946-1958.
Li et al (2010) "Serum MicroRNA Profiles Serve as Novel Biomarkers for HBV Infection and Diagnosis of HBV-Positive Hepatocarcinoma", Cancer Research 70(23): 9798-9807.
Poole et al (2011) "Virally Induced Changes in Cellular MicroRNAs Maintain Latency of Human Cytomegalovirus in CD34+ Progenitors", The Journal of General Virology 92(Pt 7): 1539-1549.
Stewart et al (2013) "Promotion of Hendra Virus Replication by MicroRNA-146a", Journal of Virology 87(7):3782-3791.
Triboulet et al (2007) "Suppression of MicroRNA-Silencing Pathway by HIV-1 During Virus Replication", Science 315(5818): 1579-1582.
GEO Expression Accession No. GPL8786, "Affymetrix miRNA Array", Published Jul. 1, 2009.
International Search Report and Written Opinion, issued Feb. 20, 2013 in connection with International Application No. PCT/AU2012/001090.
International Preliminary Report on Patentability, issued Mar. 18, 2014 in connection with International Application No. PCT/AU2012/001090.
Baeuerle and Henkel (1994) "Function and Activation of NF-κB in the Immune System", Annu. Rev. Immunol. 12:141-179.
Baldwin, A. S. (1996) "The NF-κB and IκB Proteins: New Discoveries and Insights", Annu. Rev. Immunol. 14:649-681.
Bartel, D. P. (2009) "MicroRNA Target Recognition and Regulatory Functions", Cell 136(2):215-233.
DiDonato et al. (1995) "Phosphorylation of IκBα Precedes but Is Not Sufficient for Its Dissociation from NF-κB", Mol. Cell. Biol. 15(3):1302-1311.
Driskell et al. (2009) "Quantitative Surface-Enhanced Raman Spectroscopy Based Analysis of MicroRNA Mixtures", Appl. Spectrosc. 63(10): 1107-1114.
Gardiner et al. (1989) "Practical Raman Spectroscopy", Springer-Verlag.
Hawkes, R. A. (1979) "General Principles Underlying Laboratory Diagnosis of Viral Infections", In: Lennette EHaS, N.J., editor. Washington: American Public Health Association pp. 3-48.

(Continued)

*Primary Examiner* — Amy Bowman
(74) *Attorney, Agent, or Firm* — John P. White; Cooper & Dunham LLP

(57) ABSTRACT

The present invention relates to methods of detecting an increased likelihood of virus infection in a subject. In particular, the present invention relates to methods of detecting an increased likelihood of virus infection in a subject by detecting an altered level of at least one microRNA (miRNA), as well as methods of treating or preventing virus infection. The present invention also relates to nucleotide arrays, oligonucleotides and kits useful for the detection of miRNAs associated with an increased likelihood of virus infection in a subject.

18 Claims, 7 Drawing Sheets

(56) References Cited

OTHER PUBLICATIONS

Figure 2:
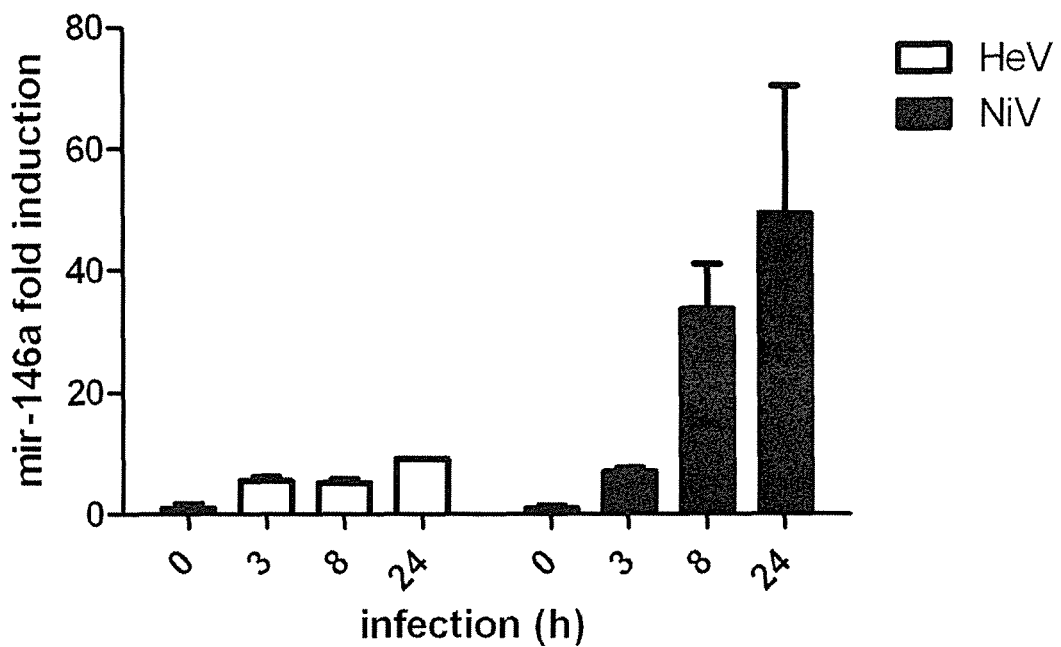

Hou et al. (2009) "MicroRNA-146a Feedback Inhibits RIG-I-Dependent Type I IFN Production in Macrophages by Targeting TRAF6, IRAK1, and IRAK2", J. Immunol. 183:2150-2158.

Kerr et al. (2011) "MicroRNAs and liver disease", Transl. Res. 157(4):241-252.

Kimmel, A. R. (1987) "Identification and Characterization of Specific Clones: Strategy for Confirming the Validity of Presumptive Clones", Methods Enzymol. 152:507-511.

Lee and Goldberg (1998) "Proteasome inhibitors: valuable new tools for cell biologists", Trends Cell. Biol. 8:397-403.

Li et al. (2010) "Serum microRNA Profiles Serve as Novel Biomarkers for HBV Infection and Diagnosis of HBV-Positive Hepatocarcinoma", Cancer Res. 70(23):9798-9807.

Liu et al. (2011) "Involvement of MicroRNAs in Lung Cancer Biology and Therapy", Transl. Res. 157(4):200-208.

Marsh et al. (2010) "Genome Sequence Conservation of Hendra Virus Isolates during Spillover to Horses, Australia", Emerg. Infect. Dis. 16(11):1767-1769.

Marsh et al. (2011) "Experimental Infection of Horses with Hendra Virus/Australia/Horse/2008/Redlands", Emerg. Infect. Dis. 17 (12) :2232-2238.

Melotti et al. (2001) "Activation of NG-κB mediates ICAM-1 induction in respiratory cells exposed to an adenovirus-derived vector", Gene Therapy 8:1436-1442.

Mitchell et al. (2008) "Circulating microRNAs as stable blood-based markers for cancer detection", Proc. Natl. Acad. Sci. 105 (30) :10513-10518.

Murray et al. (1995) "A Morbillivirus That Caused Fatal Disease in Horses and Humans", Science 268:94-97.

Nana-Sinkam and Croce (2010) "MicroRNA in chronic lymphocytic leukemia: transitioning from laboratory-based investigation to clinical application", Cancer Genet. Cytogenet. 203:127-133.

O'Connell et al. (2010) "Physiological and pathological roles for microRNAs in the immune system", Nat. Rev. Immunol. 10:111-122.

Pallister et al. (2011) "A Recombinant Hendra virus G Glycoprotein-Based Subunit Vaccine Protects Ferrets from Lethal Hendra virus Challenge", Vaccine 29(34):5623-5630.

Pierce et al. (1997) "Novel Inhibitors of Cytokine-induced IκBα Phosphorylation and Endothelial Cell Adhesion Molecule Expression Show Anti-inflammatory Effects in Vivo", J. Biol. Chem. 272(34):21096-21103.
Pranski et al. (2012) "Neuronal Ring finger protein 11 (RNF11) regulates canonical NF-κB signaling", J. Neuroinflammation 9:67.
Song et al. (2010) "In situ hybridization detection of microRNAs", Methods Mol. Biol. 629:287-294.
Taganov et al. (2006) "NF-κB-dependent induction of microRNA miR-146, an inhibitor targeted to signaling proteins of innate immune response", Proc. Natl. Acad. Sci. 103(33):12481-12486.
Wahl and Berger (1987) "Molecular Hybridization of Immobilized Nucleic Acids: Theoretical Concepts and Practical Considerations", Methods Enzymol. 152:399-407.
Wheeler et al. (2007) "In Situ Detection of Animal and Plant MicroRNAs", DNA Cell Biol. 26(4):251-255.

* cited by examiner

|        | Fold induction |       |       | P value |       |       |
| miRNA  | 3 h   | 8 h   | 24 h  | 3 h   | 8 h   | 24 h  |
| ------ | ----- | ----- | ----- | ----- | ----- | ----- |
| 151-5p | 3.65  | -1.91 | -3.74 | 0.042 | 0.34  | 0.309 |
| 146a   | 3.78  | 19.85 | 4.7   | 0.047 | 0.084 | 0.182 |
| 128    | 2.22  | -1.51 | -1.95 | 0.048 | 0.53  | 0.13  |
| 140-3p | 2.14  | 1.43  | -1.17 | 0.051 | 0.39  | 0.73  |
| 100    | 2.06  | -5.71 | -13.4 | 0.066 | 0.142 | 0.11  |
| 28-3p  | 3.05  | 1.35  | -1.47 | 0.064 | 0.53  | 0.397 |
| 302c   | -1.31 | 1.71  | 5.38  | 0.96  | 0.397 | 0.023 |
| 150    | 1.83  | 3.13  | 5.83  | 0.73  | 0.4   | 0.024 |
| 142-3p | 2.29  | 2.04  | 9.67  | 0.19  | 0.379 | 0.08  |

Figure 1

|  | TCID$_{50}$ | | | T-test* | |
|---|---|---|---|---|---|
| HeV infection | untreated | ant-146-a | ant-scramble | ant-146-a | ant-scramble |
| 8 h | 2.80 ± 5.4E-16 | 2.60 ±0.05 | 2.69 ± 0.096 | 0.027769 | 0.183503 |
| 24 h | 5.19 ±0.38 | 4.30 ±0.50 | 4.58 ± 0.25 | 0.026271 | 0.127642 |
| 48 h | 7.56 ±0.45 | 6.91 ±0.09 | 6.93 ± 0.12 | 0.176229 | 0.099626 |

*t test compared to untreated cells

Figure 5

DETECTION OF VIRAL INFECTION

CROSS-REFERENCE TO RELATED APPLICATIONS

This application is a §371 national stage of PCT International Application No. PCT/AU2012/001090, filed Sep. 13, 2012, claiming the benefit of U.S. Provisional Application No. 61/533,978, filed Sep. 13, 2011, the contents of each of which are hereby incorporated by reference in its entirety.

FIELD OF THE INVENTION

The present invention relates to methods of detecting an increased likelihood of virus infection in a subject. In particular, the present invention relates to methods of detecting an increased likelihood of virus infection in a subject by detecting an altered level of at least one microRNA (miRNA), as well as methods of treating or preventing virus infection. The present invention also relates to nucleotide arrays, oligonucleotides and kits useful for the detection of miRNAs associated with an increased likelihood of virus infection in a subject.

REFERENCE TO A SEQUENCE LISTING

This application incorporates-by-reference nucleotide and/or amino acid sequences which are present in the file named "140313_2251_86260_Substitute_Sequence_Listing_GC.txt," which is 2.82 kilobytes in size, and which was created Mar. 12, 2014 in the IBM-PC machine format, having an operating system compatibility with MS-Windows, which is contained in the text file filed Mar. 13, 2014 as part of this application.

BACKGROUND OF THE INVENTION

Together, both Nipah and Hendra viruses are members of the genus Henipavirus, a new class of virus in the Paramyxoviridae family. The mortality and morbidity associated with outbreaks of these viruses are significant and frequently severe.

In 1994, the first Australian outbreak of a highly-pathogenic virus occurred in the Brisbane suburb of Hendra. Hendra virus (HeV) (family Paramyxoviridae, genus Henipavirus) was identified as a novel causative agent (Mitchell et al., 2008). HeV is carried asymptomatically by flying foxes, and infects humans via contact with infected horses which act as an intermediary host. Since 2004, 31 outbreaks of HeV have occurred in Australia (Marsh et al., 2010), with 17 outbreaks occurring from June to August 2011. The virus is highly-pathogenic in humans (7 reported cases, 4 fatalities, mortality rate 57%), but little is known about disease pathogenesis. There are currently no licensed vaccines or therapeutics to treat HeV infections.

Nipah virus (NiV) is an emerging zoonotic virus (a virus transmitted to humans from animals) that is closely related to Hendra virus. In infected people, Nipah virus causes severe illness characterized by inflammation of the brain (encephalitis) or respiratory diseases. It can also cause severe disease in animals such as pigs, resulting in significant economic losses for farmers.

Nipah virus was first recognized in 1999 during an outbreak among pig farmers in Malaysia. Since then, there have been another 12 outbreaks, all in South Asia. Although Nipah virus has caused only a few outbreaks, it infects a wide range of animals and causes severe disease and death in people, making it a serious public health concern. There are currently no drugs or vaccines available to treat Nipah virus infection. Intensive supportive care with treatment of symptoms is the main approach to managing the infection in people.

In addition to Henipaviruses, there are a number of viruses that are capable of causing significant disease outbreaks. Outbreaks can spread very rapidly in emergency situations and lead to high morbidity and mortality rates. Thus, it is desirable to detect an outbreak as early as possible so as to control the spread of disease among the population at risk.

Thus, there remains a need for methods for diagnosing or detecting virus infection and for methods for the treatment or prevention of virus infection. In addition, there is a need for methods for the early detection of infection by viruses that cause outbreaks leading to significant morbidity and mortality.

SUMMARY OF THE INVENTION

The present inventors have found that the level of miRNAs in a subject is altered during viral infection when compared to a control sample.

Accordingly, the present invention provides a method for determining the likelihood of virus infection in a subject, the method comprising determining the level of at least one miRNA associated with virus infection in the subject, wherein an altered level of the at least one miRNA in the subject when compared to a control is indicative of an increased likelihood of virus infection.

In one embodiment, the virus is selected from Henipavirus, Ebola virus, Hantaan virus, Lassa fever virus, Marburg virus, Crimean-Congo haemorrhagic fever virus, Monkeypox virus, Rift Valley Fever virus, South American haemorrhagic fever viruses, Central European tick-borne encephalitis virus, Far Eastern tick-borne encephalitis virus, Japanese encephalitis virus, Russian spring and summer encephalitis virus, Kyasanur forest disease virus, Omsk hemorrhagic fever virus and West Nile virus.

In another embodiment, the virus is Henipavirus. In one particular embodiment, the virus is Hendra virus. In another embodiment, the virus is Nipah virus.

In one embodiment, the at least one miRNA includes a miRNA selected from miR-151-5p, miR-146a, miR-128, miR-140-3p, miR-100, miR-28-3p, miR-302c, miR-150 and/or miR142-3p. In one particular embodiment, the miRNA comprises a nucleotide sequence at least 95% identical to any one of SEQ ID Nos:6 to 14. In another embodiment, the miRNA comprises or consists of a nucleotide sequence that is identical to any one of SEQ ID Nos:6 to 14.

While the miRNA associated with virus infection may be increased or decreased at any given stage of infection when compared to a control, in one embodiment, the level of the at least one miRNA is increased when compared to the control. In one embodiment, the at least one miRNA that is increased is selected from miR-146a, miR-150 and/or miR-142-3p.

In another embodiment, the miRNA is selected from miR-146a and/or miR-100.

In one embodiment, the at least one miRNA is miR-146a. In one particular embodiment, miR-146a comprises a nucleotide sequence at least 95% identical to SEQ ID NO:7. In another embodiment, miR-146a comprises or consists of a nucleotide sequence identical to SEQ ID NO:7.

The methods of the invention may comprise determining the level of a miRNA associated with virus infection in a sample obtained from the subject. In one embodiment, the sample is selected from blood, urine, rectal swab, oral swab, nasal swab and/or faeces. In one particular embodiment, the method comprises determining the level of the at least one miRNA in a blood sample obtained from the subject.

Any suitable method for detecting miRNA in a sample may be used in the methods of the invention. In one embodiment, the method comprises amplifying the miRNA. In one particular embodiment, the miRNA is amplified by quantitative reverse transcription polymerase chain reaction.

In another embodiment, the miRNA may be detected in a sample by spectroscopy. In one specific example, the miRNA is detected by Raman spectroscopy.

The skilled person will appreciate that the methods of the invention are useful for determining an increased likelihood of virus infection in any animal that is susceptible to infection by a given virus. Thus, in one embodiment, the subject is a non-human animal such as, but not limited to, a domesticated animal such as a horse, pig, sheep, bovine, chicken or dog. In another embodiment, the subject is a bat or a ferret. In yet another embodiment, the subject is a human. In one particular embodiment, the subject is a horse.

The methods of the present invention advantageously allow for the identification of subjects having an increased likelihood of virus infection at a time point before virus can be detected by prior art methods. Accordingly, in one embodiment, the method of the invention is performed before virus is detectable in a sample from the subject.

In one embodiment, the method further comprises diagnosing virus infection in the subject.

In one embodiment, diagnosing virus infection comprises detecting a viral polypeptide, viral polynucleotide, viral particle and/or antibody to a viral polypeptide in a subject sample.

In one particular embodiment, diagnosing virus infection comprises performing ELISA, PCR, immunofluorescence assay, serum neutralisation test and/or virus isolation.

The present invention further provides a method of detecting virus replication in a biological sample obtained from a subject, the method comprising detecting in the sample a level of at least one miRNA associated with virus infection, wherein an altered level of the at least one miRNA in the sample when compared to a control is indicative of virus replication.

In one embodiment, the at least one miRNA is selected from miR-151-5p, miR-146a, miR-128, miR-140-3p, miR-100, miR-28-3p, miR-302c, miR-150 and/or miR142-3p.

The present invention further provides a method of treatment comprising performing the method for determining the likelihood of virus infection of the invention and administering a therapeutic agent for the treatment of virus infection or a symptom of virus infection.

The present invention further provides a nucleotide array for determining the likelihood of virus infection in a subject, the microarray comprising miRNA-specific probes for at least one miRNA associated with virus infection.

In one embodiment, the miRNA is selected from miR-151-5p, miR-146a, miR-128, miR-140-3p, miR-100, miR-28-3p, miR-302c, miR-150 and/or miR142-3p.

The present invention further provides a set of oligonucleotides for amplifying at least one miRNA associated with virus replication, wherein the at least one miRNA is selected from miR-151-5p, miR-146a, miR-128, miR-140-3p, miR-100, miR-28-3p, miR-302c, miR-150 and/or miR142-3p.

The present invention further provides a kit comprising a nucleotide array for determining the likelihood of virus infection in a subject, the nucleotide array comprising miRNA-specific probes for at least one miRNA selected from miR-151-5p, miR-146a, miR-128, miR-140-3p, miR-100, miR-28-3p, miR-302c, miR-150 and/or miR142-3p.

The present invention further provides a kit comprising a set of oligonucleotides for amplifying at least one miRNA associated with virus replication, where the at least one miRNA is selected from miR-151-5p, miR-146a, miR-128, miR-140-3p, miR-100, miR-28-3p, miR-302c, miR-150 and/or miR142-3p.

In one embodiment, the kit further comprises a control sample.

The present invention further provides a method of treating or preventing virus infection in a subject, the method comprising administering to the subject an antagonist of at least one miRNA associated with virus infection.

In one embodiment, the at least one miRNA is selected from miR-151-5p, miR-146a, miR-128, miR-140-3p, miR-100, miR-28-3p, miR-302c, miR-150 and/or miR142-3p. In one particular embodiment, the miRNA associated with virus infection comprises a nucleotide sequence at least 95% identical to any one of SEQ ID Nos:6 to 14. In another embodiment, the miRNA associated with virus infection comprises or consists of a nucleotide sequence identical to any one of SEQ ID Nos:6 to 14.

In one embodiment of the method of treating or preventing virus infection in a subject, the virus is selected from Henipavirus, Ebola virus, Hantaan virus, Lassa fever virus, Marburg virus, Crimean-Congo haemorrhagic fever virus, Monkeypox virus, Rift Valley Fever virus, South American haemorrhagic fever viruses, Central European tick-borne encephalitis virus, Far Eastern tick-borne encephalitis virus, Japanese encephalitis virus, Russian spring and summer encephalitis virus, Kyasanur forest disease virus, Omsk hemorrhagic fever virus and West Nile virus.

In another embodiment of the method of treating or preventing virus infection in a subject, the virus is Henipavirus. In one particular embodiment, the virus is Hendra virus. In another embodiment, the virus is Nipah virus.

In yet another embodiment, the antagonist is an oligonucleotide comprising a nucleotide sequence complementary to the miRNA.

In the method of treatment or prevention of the invention, the subject may be a human. Alternatively, the subject may be a non-human animal such as a horse, pig, dog, sheep, bovine, chicken, bat or ferret.

In one embodiment, the antagonist targets a miRNA, wherein the level of the miRNA is increased during virus infection in the absence of the antagonist.

In one embodiment, the antagonist is directed to a miRNA selected from miR-146a, miR-150 and/or miR-142-3p.

In another embodiment, the miRNA is selected from miR-146a and/or miR-100.

In another embodiment, the method comprises administering to the subject an antagonist of at least one miRNA associated with virus infection and an NF-κB inhibitor.

In yet another embodiment, the method comprises performing the method for determining the likelihood of virus infection in a subject of the invention prior to administering the antagonist to the subject.

The present invention further provides a method of treating or preventing virus infection in a subject, the method comprising administering to the subject an NF-κB inhibitor.

In one embodiment, the virus is Henipavirus. In one particular embodiment, the virus is Hendra virus. In another embodiment, the virus is Nipah virus.

In the method of the treatment or prevention of virus infection in a subject, the subject may be a human. Alternatively, the subject may be a non-human animal such as a horse, pig, dog, sheep, bovine, chicken, bat or ferret.

The present invention further provides use of an antagonist of a miRNA associated with virus infection in the manufacture of a medicament for the treatment or prevention of virus infection.

In one embodiment, there is provided use of an antagonist of a miRNA associated with Henipavirus infection in the manufacture of a medicament for the treatment or prevention of Henipavirus infection.

The present invention further provides use of an antagonist of a miRNA associated with virus infection and an NF-κB inhibitor in the manufacture of a medicament for the treatment or prevention of virus infection.

In one embodiment, there is provided use of an antagonist of a miRNA associated with Henipavirus infection and an NF-κB inhibitor in the manufacture of a medicament for the treatment or prevention of Henipavirus infection.

The present invention further provides an antagonist of a miRNA associated with virus infection for use in the treatment or prevention of virus infection.

In one embodiment, there is provided an antagonist of a miRNA associated with Henipavirus infection for use in the treatment or prevention of Henipavirus infection.

The present invention further provides an atagonist of a miRNA associated with virus infection and an NF-κB inhibitor for use in the treatment or prevention of virus infection.

In one embodiment, there is provided an atagonist of a miRNA associated with virus infection and an NF-κB inhibitor for use in the treatment or prevention of Henipavirus infection.

The present invention further provides a pharmaceutical composition comprising an antagonist of a miRNA associated with virus infection and a pharmaceutically acceptable carrier or excipient.

In one embodiment, the pharmaceutical composition further comprises an NF-κB inhibitor.

In one embodiment the virus infection is Henipavirus infection. In one particular embodiment, the virus infection is Hendra virus infection. In another embodiment, the virus infection is Nipah virus infection.

In one embodiment, the antagonist of a miRNA associated with virus infection is an antagomir.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. miRNAs that were identified as differentially regulated by HeV infection in Hela cells.

FIG. 2. Hela cells infected with Hendra virus (white bars) or Nipah virus (black bars) at a multiplicity of infection (m.o.i.) of 2 of indicated time periods. miR-146a levels were quantitated by qPCR and normalised against human GAPDH.

Figure 3:
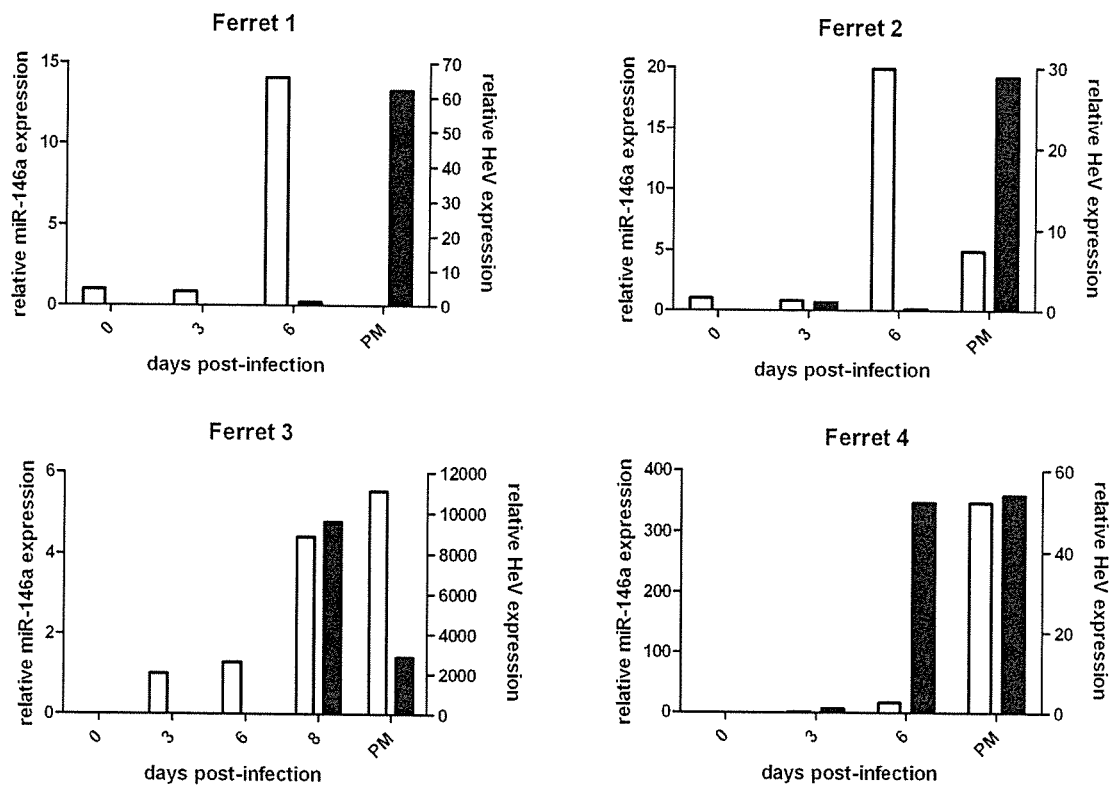

FIG. 3. Relative levels of mir-146a (white bars) and HeV genome (black bars) in whole blood from ferrets infected with HeV. PM—post-mortem.

Figure 4:
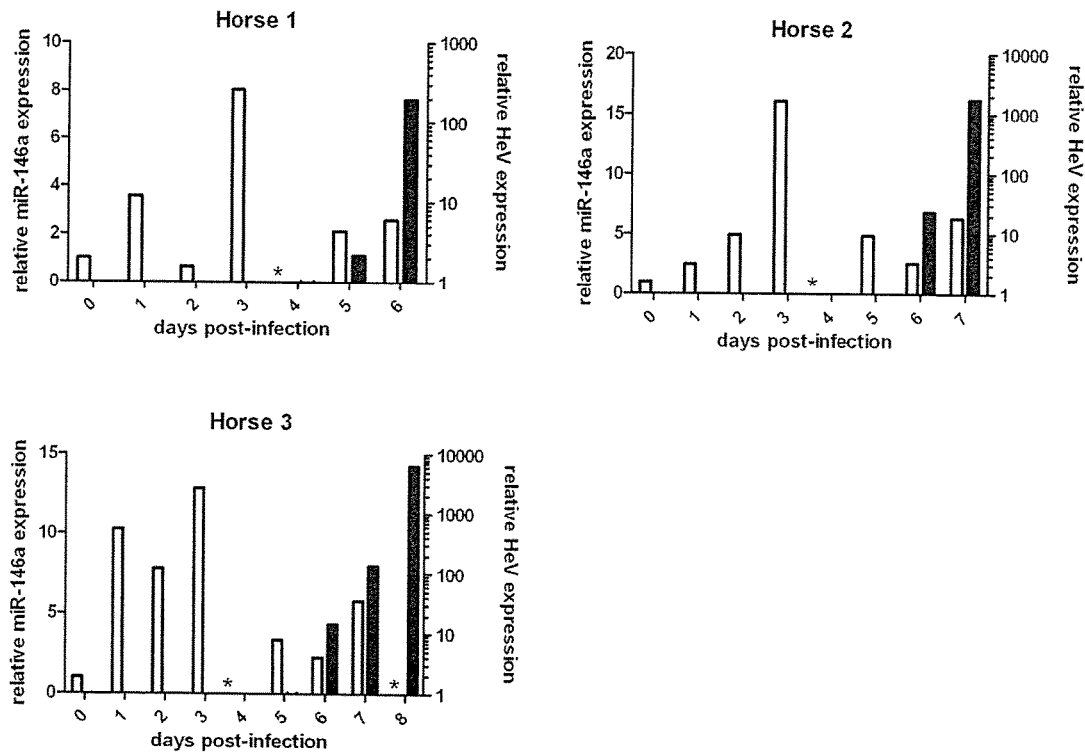

FIG. 4. Relative expression levels of mir-146a (white bars) and HeV (black bars) in whole blood of horses infected with HeV. *=PCR not successful for these samples.

FIG. 5. Replication of HeV in Hela cells measured over a 48 hour time course by TCID50 assay.

Figure 6:
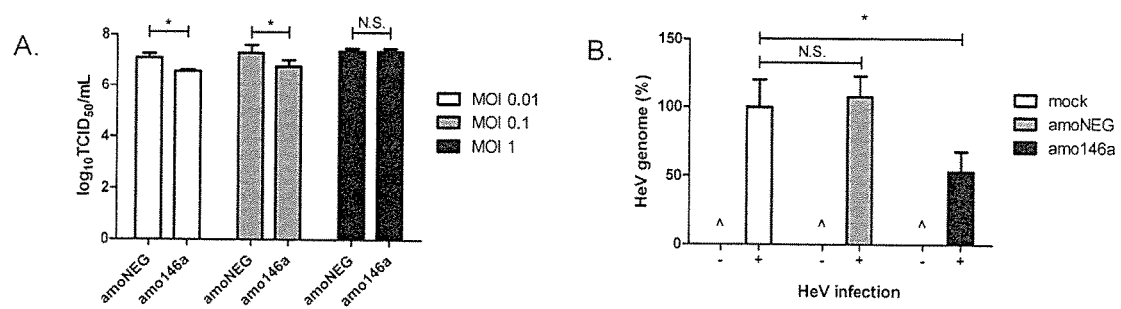

FIG. 6. (A) TCID50 measurement of Hendra virus titres in HeLa cell supernatants of cells treated with a miR-146a specific inhibitor or a negative control miRNA inhibitor (both 200 nM) and infected with Hendra virus for 24 h. (B) Hendra virus genome detected by QRT-PCR in HeLa cells treated as in (A), followed by Hendra virus infection (MOI 0.1 for 24 h).

Figure 7:
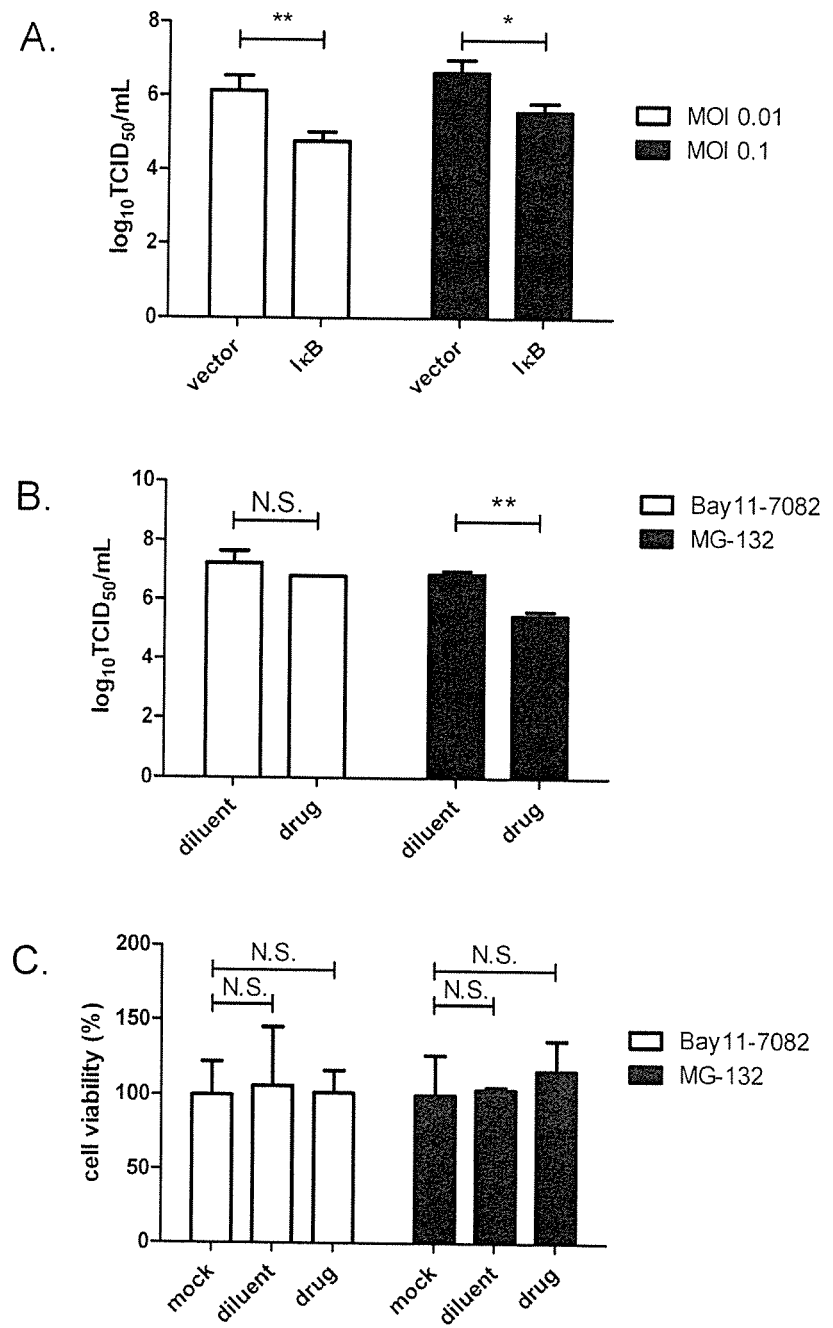

FIG. 7. Inhibition of NF-κB activity suppresses Hendra virus replication. (A) HeV titres from HeLa cells transfected with pCMV-MAD-3 (vector) or vector containing RNF11 and infected with HeV (24 h). (B) HeV titres from HeLa cells pre-treated for 1 h with Bay11-7082 (1 mM) or MG-132 (10 mM) or appropriate diluent, followed by HeV infection for 24 h (MOI 0.1). (C) Viability of HeLa cells treated with Bay11-7082 (1 mM) or MG-132 (10 mM) for 25 h. Mock refers to untreated cells

KEY TO SEQUENCE LISTING

SEQ ID NO:1—Oligonucleotide primer
SEQ ID NO:2—Oligonucleotide primer
SEQ ID NO:3—Oligonucleotide primer
SEQ ID NO:4—mir-146a antagomir
SEQ ID NO:5—control antagomir
SEQ ID NO:6—miR-151-5p
SEQ ID NO:7—miR-146a
SEQ ID NO:8—miR-128
SEQ ID NO:9—miR-140-3p
SEQ ID NO:10—miR-100
SEQ ID NO:11—miR-28-3p
SEQ ID NO:12—miR-302c
SEQ ID NO:13—miR-150
SEQ ID NO:14—miR142-3p

DETAILED DESCRIPTION

General Techniques and Definitions

Unless specifically defined otherwise, all technical and scientific terms used herein shall be taken to have the same meaning as commonly understood by one of ordinary skill in the art (e.g. molecular biology, molecular genetics, virology, immunology, immunohistochemistry, protein chemistry, and biochemistry).

Unless otherwise indicated, the molecular biology, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The "subject" may be any animal that is susceptible to infection with Henipavirus. For example, the subject may be a mammal such as, but not limited to, a domesticated animal such as a pig, horse or dog, or alternatively the subject may be a bat or a ferret. In one embodiment, the subject is a human.

The "sample" may be of any suitable type and may refer to, for example, a sample from a subject containing miRNAs. Preferably, the sample is obtained from the subject so that methods of determining an increased likelihood of Henipavirus infection may be performed in vitro. For example, the sample may be a sample of tissue or organ. Alternatively, the methods of the invention may be performed in vivo. The sample can be used as obtained directly from the source or following at least one step of (partial) purification. The sample can be prepared in any convenient medium which does not interfere with the method of the invention. Typically, the sample is an aqueous solution, biological fluid, cells or tissue. Pre-treatment may involve, for example, diluting viscous fluids, and the like. Treatment of a sample can involve filtration, distillation, separation, concentration, inactivation of interfering components, and the addition of reagents. The selection and pre-treatment of biological samples prior to testing is well known in the art and need not be described further. In one embodiment, the sample is a blood, urine, rectal swab, oral swab, nasal swab and/or faeces sample obtained from the subject.

"Administering" as used herein is to be construed broadly and includes administering an agent to a subject as well as providing an agent to a cell.

As used herein, the terms "treating", "treat" or "treatment" include administering a therapeutically effective amount of an agent sufficient to reduce or delay the onset or progression of Henipavirus infection, or to reduce or eliminate at least one symptom of Henipavirus infection.

As used herein, the terms "preventing", "prevent" or "prevention" include administering a therapeutically effective amount of an agent to stop or hinder the development of at least one symptom of Henipavirus infection.

MicroRNAs

MicroRNAs (miRNAs) are small single-stranded non-coding RNAs that play critical roles in the regulation of biological processes (reviewed in Bartel, 2009). First identified in *Caenorhabditis elegans* in 1993, it is estimated that the human genome contains more than 700 miRNAs, with each miRNA potentially capable of regulating many, perhaps hundreds, of target mRNAs. miRNAs regulate gene expression by repressing target genes at the post-transcriptional level via the RNA interference (RNAi) pathway.

MicroRNAs are initially transcribed as a long, single-stranded miRNA precursor known as a primary-miRNA (pri-miRNA), which may contain one or several miRNAs. These pri-miRNAs typically contain regions of localized stem-loop hairpin structures that contain the mature miRNA sequences. Pri-miRNAs are processed into 70-100 nucleotide pre-miRNAs in the nucleus by the double-stranded RNA-specific nuclease Drosha. These 70-100 nucleotide pre-miRNAs are transported to the cytoplasm, where they are processed by the enzyme Dicer into single-stranded mature miRNAs of about 19-25 nucleotides.

Following processing, mature miRNAs are incorporated into a RISC (RNA-Induced Silencing Complex), which participates in RNA interference (RNAi). miRNAs have been shown to be important modulators of cellular pathways including growth and proliferation, apoptosis, and developmental timing. Given the pathways over which miRNAs exert a regulatory effect, it is not surprising that alterations in miRNA expression have been detected in several types of cancer, including breast and lung carcinomas. The present inventors have now investigated the role of host miRNAs in virus infection.

By investigating the level of miRNAs in cells and various samples from animals infected with virus, the present inventors demonstrate that the level of certain miRNAs are altered as a result of viral infection when compared to a control sample. As used herein, the phrase "miRNA associated with virus infection in a subject" refers to a miRNA the level of which is altered in a subject, tissue or cell as a result of virus invention when compared to a subject, tissue or cell in the absence of the virus. Accordingly, the phrase "miRNA associated with Henipavirus infection" refers to a miRNA the level of which is altered in a subject, tissue or cell as a result of Henipavirus infection when compared to a subject, tissue or cell in the absence of the virus.

Detection of miRNAs

Any suitable technique that allows for the qualitative and/or quantitative assessment of the level of a miRNA in a sample, such as a biological sample from a subject, may be used. Comparison may be made by reference to a standard control, or to a control level that is found in a sample from a healthy subject. For example, levels of a miRNA can be determined by Northern blotting, and/or RT-PCR. With the advent of quantitative (real-time) PCR, quantitative analysis of the level of miRNAs can be achieved by using appropriate primers for the miRNA of interest. The nucleic acid may be labelled and hybridised on a nucleotide array, or microarray, in which case the miRNA concentration will be directly proportional to the intensity of the radioactive or fluorescent signal generated in the array. In another embodiment, miRNA levels are determined by spectroscopy, such as by Raman spectroscopy.

In one particular example, a likelihood of infection with a virus in a subject may be determined by contacting nucleic acid in a subject sample with a nucleic acid probe under stringent hybridisation conditions that allow the formation of a hybrid complex between the nucleic acid probe and a miRNA and detecting the presence of a hybrid complex in the sample. It may be preferable to label the nucleic acid probe to aid its detection. The level of detection is compared to control levels, such as, for example, miRNA levels from a healthy subject or a standard control. Detection of altered levels of the hybrid complex from the subject sample is indicative of a likelihood of infection with a Henipavirus.

The term "hybridization" or variants thereof as used here refers to the association of two nucleic acid molecules with one another by hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. Molecular Cloning; A Laboratory Manual, Third Edition (2001)). In accordance with these principles, the inhibition of hybridization of a complementary molecule to a target molecule may be examined using a hybridization assay; a substantially homologous molecule possessing a greater degree of homology will then compete for and inhibit the binding of a completely homologous molecule to the target molecule under various conditions of stringency, as taught in Wahl and Berger (1987) and Kimmel (1987).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate, pH8.0), 50 mM sodium phosphate (pH7.6), 5×Denhardt's solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. Preferably, the conditions used for hybridization in the methods of the present invention are those of high stringency.

The nucleic acid may be separated from the sample for testing. Suitable methods will be known to those of skill in the art. For example, RNA may be isolated from a cell sample to be analysed using conventional procedures, such as by homogenization in the presence of nucleic acid extraction buffer, for example, as are supplied by QIAGEN technology, followed by centrifugation. Nucleic acids are precipitated, and DNA is removed by treatment with DNase and precipitation.

Diagnostic procedures may also be performed directly upon patient samples. Hybridisation or amplification assays, such as, for example, Southern or Northern blot analysis, immunohistochemistry, single-stranded conformational polymorphism analysis (SSCP) and PCR analyses are among techniques that are useful in this respect. If desired, target or probe nucleic acid may be immobilised to a solid support such as a microtitre plate, membrane, polystyrene bead, glass slide or other solid phase.

Suitable probes for Northern blot hybridization of a given miRNA can be produced using the nucleotide sequence of a miRNA. In one embodiment, probes are produced using the nucleic acid sequences of human, equine, porcine, murine, bovine or avian corresponding to the miRNAs described herein. The nucleic acid sequences corresponding to the miRNAs are also available on miRBase (mirbase.org).

Methods for preparation of labeled DNA and RNA probes, and the conditions for hybridization thereof to target nucleotide sequences, are described in, for example, Sambrook et al., (2001).

The nucleic acid probe can be labeled with, for example, a radionuclide such as $^3H$, $^{32}P$, $^{33}P$, $^{14}C$, or $^{35}S$; a heavy metal; or a ligand capable of functioning as a specific binding pair member for a labeled ligand (for example, biotin, avidin or an antibody), a fluorescent molecule, a chemiluminescent molecule, an enzyme or the like. Probes can be labeled to high specific activity using methods known in the art.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl) deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce colour reactions.

In addition to Northern and other RNA blotting hybridization techniques, determining the levels of miRNA can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (for example, cDNA or RNA) probes. This technique is well-suited for analyzing tissue biopsy samples from subjects. The practice of the in situ hybridization technique for detecting miRNA is described in the art (see, for example, Wheeler et al., 2007; Song et al., 2010).

The relative number of miRNA gene transcripts in cells can also be determined by reverse transcription of miRNA transcripts, followed by amplification of the reverse-transcribed transcripts by polymerase chain reaction (RT-PCR). The levels of miRNA transcripts can be quantified in comparison with an internal standard, for example, the level of mRNA from a "housekeeping" gene present in the same sample. A suitable "housekeeping" gene for use as an internal standard includes, for example, myosin or glyceraldehyde-3-phosphate dehydrogenase (GAPDH). The methods for quantitative RT-PCR and variations thereof are within the skill in the art.

In some embodiments, it is desirable to simultaneously determine the expression level of a plurality of different of miRNAs in a sample. In certain instances, it may be desirable to determine the expression level of the transcripts of all known miRNAs associated with virus infection. Assessing expression levels for hundreds of miRNAs can be time consuming and require a large amount of total RNA. To overcome these limitations, an oligolibrary in nucleotide array format, such as a microarray, may be constructed containing a set of probe oligonucleotides specific for a set of miRNAs. In one embodiment, the nucleotide array contains probes corresponding to all known miRNAs from the human, horse, pig, avian and/or bat genome. In alternate embodiments, the nucleotide array contains probes corresponding to all known miRNAs from the human, horse, porcine, avian or bat genomes.

The nucleotide array is prepared from miRNA-specific oligonucleotide probes generated from known miRNAs. According to one embodiment, the array contains two different oligonucleotide probes for each miRNA, one containing the active sequence and the other being specific for the precursor of the miRNA. The array may also contain controls such as one or more (e.g. mouse) sequences differing from (e.g. human) orthologs by only a few bases, which can serve as controls for hybridization stringency conditions. tRNAs from both species may also be printed on the nucleotide array, providing an internal, relatively stable positive control for specific hybridization. One or more appropriate controls for non-specific hybridization may also be included on the nucleotide array. For this purpose, sequences are selected based upon the absence of any homology with any known miRNAs.

The nucleotide array, for example, a microarray, may be fabricated by techniques known in the art. For example, probe oligonucleotides of an appropriate length, e.g., 40 nucleotides, may be 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target miRNAs is prepared by reverse transcribing the target miRNA with labeled primer. Following first strand synthesis, the RNA/DNA hybrids are denatured to degrade the RNA templates. The labeled target cDNAs thus prepared are then hybridized to the microarray chip under hybridizing conditions, for example, 6×SSPE/ 30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRNAs, in the sample. According to one embodiment, the labeled cDNA oligomer is a biotin-labeled cDNA, prepared from a biotin-labeled primer. The microarray is then processed by direct detection of the biotin-containing transcripts using, for example, Streptavidin-Alexa647 conjugate, and scanned utilizing conventional scanning methods. The intensity of each spot on the array is proportional to the abundance of the corresponding miRNA in the sample.

In one embodiment of the invention, the at least one miRNA is detected by spectroscopy, preferably Raman spectroscopy. Raman spectroscopy is a spectroscopic technique used to study vibrational, rotational, and other low-frequency modes in a system (Gardiner, 1989; Driskell et al., 2009). It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system. Infrared spectroscopy yields similar, but complementary, information.

Preferably, a miRNA that is detected in a method of the invention has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% identical, or any range derivable therein, to the 5' to 3' sequence of a mature miRNA, particularly an endogenous miRNA, and/or to any one of the miRNA sequences provided as SEQ ID NOs:6 to 14.

Detection or Diagnosis of Viral Infection

Based on the findings of the present inventors, the likelihood of virus infection in a subject can be determined by determining the level of at least one miRNA that is associated with virus infection in a subject sample. The finding of an altered level of at least one miRNA in the subject when compared to a control is indicative of an increased likelihood of virus infection.

The methods of the invention can be used to determine the likelihood of virus infection, wherein the virus is selected from Henipavirus, Ebola virus, Hantaan virus, Lassa fever virus, Marburg virus, Crimean-Congo haemorrhagic fever virus, Monkeypox virus, Rift Valley Fever virus, South American haemorrhagic fever viruses, Central European tick-borne encephalitis virus, Far Eastern tick-borne encephalitis virus, Japanese encephalitis virus, Russian spring and summer encephalitis virus, Kyasanur forest disease virus, Omsk hemorrhagic fever virus and West Nile virus.

As used herein, the phrase "determining the likelihood of virus infection" and variants thereof refer to determining whether a subject is more likely or has an increased risk of being infected with a virus when compared to a healthy individual. In the present context, the term "healthy individual" shall be taken to mean an individual who is known not to be infected with a virus, such knowledge being derived from clinical data on the individual, including, but not limited to, a different diagnostic assay to that described herein.

The present inventors have found advantageously that the detection of miRNAs associated with virus infection allows for the identification of subjects that are likely infected with virus before virus is detectable by standard techniques. Accordingly, as used herein, the phrase "before virus is detectable" and variants thereof refers to the early stages of virus infection in which prior art diagnostic techniques are unable to detect virus. Such standard techniques include ELISA, PCR, immunofluorescence assay, serum neutralisation test and/or virus isolation. Thus, the methods of the invention provide the earliest indication yet known of virus infection. The early detection of subjects with an increased likelihood of virus infection will be valuable in the early management of virus outbreaks, for example, by allowing for the identification and quarantining of humans and animals suspected of being infected.

The skilled person will appreciate that the detection of at least one miRNA associated with virus infection in a subject may not necessarily be determinative of virus infection. Thus, it may be desirable to perform other conventional diagnostic techniques once an individual has been identified as having an increased likelihood of virus infection. For example, once a subject has been identified as having an increased likelihood of virus infection using the methods of the invention, it may be desirable to diagnose virus infection using a conventional technique such as ELISA, PCR, immunofluorescence assay, serum neutralisation test and/or virus isolation. The skilled person will understand that if the methods of determining an increased likelihood of viral infection are performed at an early point in viral infection, a diagnostic test may need to be performed over one or more days, for example up to three, four or five days, before the virus infection can successfully be diagnosed using prior art methods.

In the methods of the invention, suitable controls may be included when performing the method of the invention. Such suitable controls will be known to one skilled in the art and are considered part of the common knowledge. The relative miRNA expression in the control or normal samples can further be determined with respect to one or more RNA expression standards. The standards can comprise, for example, a zero miRNA level, the miRNA level in a standard cell line, or the average level of miRNA previously obtained for a population of normal human or animal controls.

As will be known to those skilled in the art, when internal controls are not included, the control may be derived from an established data set.

Data pertaining to the control subjects are preferably selected from the group consisting of:

1. a data set comprising measurements of the presence or level of expression of miRNA for a typical population of subjects known to have a virus infection;

2. a data set comprising measurements of the presence or level of expression of miRNA for the subject being tested wherein said measurements have been made previously, such as, for example, when the subject was known to be healthy or, in the case of a subject suspected of having a virus infection, when the subject was diagnosed or at an earlier stage in disease progression;

3. a data set comprising measurements of the presence or level of expression of miRNA for a healthy individual or a population of healthy individuals; and 4. a data set comprising measurements of the presence or level of expression of miRNA for a normal individual or a population of normal individuals.

In the present context, the term "typical population" with respect to subjects known to have a virus infection shall be taken to refer to a population or sample of subjects diagnosed with virus infection that is representative of the spectrum of the patients. This is not to be taken as requiring a strict normal distribution of morphological or clinicopathological parameters in the population, since some variation in such a distribution is permissible. Preferably, a "typical population" will exhibit a spectrum of the virus infection at different stages of disease progression.

As will be known to those skilled in the art, data obtained from a sufficiently large sample of the population will normalize, allowing the generation of a data set for determining the average level of miRNA expression in a sample from a subject.

Those skilled in the art are readily capable of determining the baseline for comparison in the method of the present invention without undue experimentation, based upon the teaching provided herein.

Therapeutic Applications

The present inventors have found that blocking of a miRNA associated with virus infection results in a decrease in viral replication in virus infected cells. Accordingly, the present invention provides a method of treating or preventing virus infection in a subject, the method comprising administering to the subject an antagonist of at least one miRNA associated with virus infection. Preferably, the antagonist decreases the level or replication of the virus in cells or tissue of the subject by at least 5%, 10%, 33%, 50%, 75%, 90%, 95% or 99% as compared to the level or replication of the virus in the absence of the antagonist.

miRNA Antagonists miRNA antagonists suitable for use in the methods of the invention include any compound or agent that is capable of modulating the level or activity of a miRNA in a cell or tissue of a subject. Thus, a "miRNA antagonist" as used herein includes reference to an oligonucleotide that specifically inhibits a miRNA by binding to it and/or by interfering with the activity of the miRNa. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides may be used over native forms because of desirable properties such as, for example, enhanced cellular uptake, enhanced affinity for nucleic acid target, and/or increased stability in the presence of nucleases. The miRNA inhibitory nucleic acids include oligomers or polymers of ribonucleic acid (RNA) or deoxyribonucleic acid (DNA) or both, or modifications thereof. The miRNA inhibitory nucleic acid can be a single-stranded, double stranded, partially double stranded or hairpin oligonucleotide. It preferably consists of, consists essentially of, or comprises at least 12 or more contiguous nucleotides substantially complementary to an endogenous miRNA or a pre-miRNA. As used herein "partially double stranded" refers to double stranded structures that contain fewer nucleotides on one strand. In general, such partial double stranded agents will have less than 75% double stranded structure, less than 50%, or less than 25%, 20% or 15% double stranded structure.

A miRNA antagonist may comprise a region sufficient complementary to the target nucleic acid (e.g., target miRNA, pre-miRNA), and is of sufficient length, such that the miRNA inhibitory nucleic acid forms a duplex with the target nucleic acid. The miRNA antagonist can modulate the function of the targeted molecule. For example, when the target molecule is a miRNA, such as for example mir-146a, the miRNA antagonist can inhibit the gene regulatory activity of the target miRNA, which action will alter expression of the mRNA targeted by the target miRNA.

A miRNA antagonist can be partially or fully complementary to the target miRNA. It is not necessary that there be perfect complementarity between the miRNA antagonist and the target, but the correspondence must be sufficient to enable the miRNA antagonist to modulate target gene expression. The miRNA antagonist and the target miRNA can have mismatched complementarity at 1, 2, 3, 4, or 5 nucleotide positions.

The miRNA antagonist can be about 12 to about 33 nucleotides long, preferably, about 15 to about 25, or about 18 to about 25 nucleotides long, or about 21-33 nucleotides long. In certain embodiments, a miRNA antagonist molecule is 12, 13, 14, 15, 16, 17, 18, 19, 20, 21, 22, 23, 24, 25, 26, 27, 28, 29, 30, 31, 32, or 33 nucleotides in length, or any range derivable therein. Moreover, a miRNA antagonist has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly an endogenous miRNA, and/or to any one of the miRNA sequences provided as SEQ ID NOs:6 to 14.

The miRNA antagonist can be further stabilized against nucleolytic degradation such as by the incorporation of a modification, for example, a nucleotide modification. The miRNA antagonist acid may include a phosphorothioate at the first, second, or third internucleotide linkage at the 5' or 3' end of the nucleotide sequence. In one embodiment, the miRNA antagonist includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a particular embodiment, the miRNA antagonist includes at least one 2'-O-methyl-modified nucleotide, and in some embodiments, all of the nucleotides of the miRNA antagonist include a 2'-O-methyl modification.

The miRNA antagonist can be modified so as to be attached to a ligand that is selected to improve stability, distribution or cellular uptake of the agent, for example, cholesterol. The oligonucleotide miRNA antagonist can further be in isolated form or can be part of a pharmaceutical composition used for the methods described herein, particularly as a pharmaceutical composition formulated for parenteral administration. The pharmaceutical compositions can contain one or more oligonucleotide agents, and in some embodiments, will contain two or more oligonucleotide agents, each one directed to a different miRNA.

Antagomirs are a specific class of miRNA antagonists that are described, for example, in US 2007/0213292. Antagomirs are RNA-like oligonucleotides that contain various modifications for RNase protection and pharmacologic properties such as enhanced tissue and cellular uptake. Antagomirs differ from normal RNA by having complete 2'-O-methylation of sugar, phosphorothioate backbone and a cholesterol-moiety at 3'-end.

NF-κB Inhibitors

The mammalian nuclear transcription factor, NF-κB, is a multi-subunit complex involved in the activation of gene transcription, including the regulation of apoptosis (programmed cell death) (Baeuerle and Henkel, 1994; Baldwin, 1996). NF-κB exists mainly as a homodimer (p50/p50) or heterodimer (p50/p65) in the cytoplasm in the form of an inactive complex with the inhibitory IκB protein. Cellular stimuli including anti-neoplastic agents and inflammatory cytokines result in the IKK mediated phosphorylation of IκB on serines 32 and 36, followed by ubiquitination and subsequent degradation by the 26S proteosome. Degradation of IκB ensures the release of NF-κB. Upon release, NF-κB translocates into the nucleus where the subunits bind with specific DNA control elements and initiates gene transcription.

The present inventors have now shown that modulation of NF-κB activity affects Hendra virus replication. Accordingly, NF-κB inhibitors can be used alone or in combination with miRNA antagonists in the treatment or prevention of viral infection. The skilled person will appreciate that in the method of the invention a miRNA antagonist and an NF-κB inhibitor may be administered together in a single composition or in separate compositions. The skilled person would understand that when the miRNA antagonist and an NF-κB inhibitor are provided in separate compositions, they may be administered at the same time, or they may be administered separately with either the miRNA antagonist or NF-κB inhibitor administered at a first time point, and followed by the other at a suitable second time point.

In the method of the invention, any suitable NF-κB inhibitory molecule can be used. Examples of NF-κB inhibitory molecules include chemical inhibitors including Bay11-7082 (ref) and MG-132 (ref). Other examples of NF-κB inhibitory molecules include N-acetyl-L-cysteine, pyrrolidine dithiocarbamate, parthenolide, as well as those described in US 20070031410; or for example, a therapeutically effective amount of a curcumin derivative as described in US 20060258752. In alternative embodiments, NF-κB may be inhibited, for example, by inhibiting CARD11 nucleic acids as described in US 20040072228 or by increasing the amount of or activating an IκB.

In an alternative embodiment, the inhibitor of NF-κB is SN50. This peptide comprises a nuclear localization sequence (NLS) for NF-κB linked to a cell-permeable carrier. SN50 can inhibit NF-κB by interfering with its translocation through the nuclear pore (Melotti et al., 2001).

Pharmaceutical Compositions

Compositions comprising an antagonist of a miRNA associated with virus infection together with a pharmaceutically acceptable carrier or excipient are useful in the therapeutic or prophylactic methods of the present invention. Pharmaceutical compositions can be prepared by mixing the desired therapeutic agent having the appropriate degree of purity with optional pharmaceutically acceptable carriers, excipients, or stabilizers (Remington's Pharmaceutical Sciences, 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Kits

The present invention provides kits for determining an increased likelihood of virus infection in a subject. Such kits are suitable for the detection of nucleic acid species such as miRNA. The kits of the invention will preferably comprise a nucleotide array comprising miRNA-specific probes and/or oligonucleotides for amplifying at least one miRNA associated with virus infection in a subject. Optionally, a kit according to the invention may comprise one or more control samples.

For detection of nucleic acids, such kits may contain a first container such as a vial or plastic tube or a microtiter plate that contains an oligonucleotide probe. The kits may optionally contain a second container that holds primers. The probe may be hybridisable to a miRNA or DNA reverse transcribed from the miRNA whose altered level is associated with an increased likelihood of Henipavirus infection. In one embodiment, the primers are useful for amplifying DNA. Kits that contain an oligonucleotide probe immobilised on a solid support could also be developed, for example, using arrays (see supplement of issue 21(1) Nature Genetics, 1999).

For PCR amplification of nucleic acid, nucleic acid primers may be included in the kit that are complementary to at least a portion of a miRNA or DNA reverse transcribed from a miRNA as described herein. The set of primers typically includes at least two oligonucleotides, alternatively four oligonucleotides, that are capable of specific amplification of DNA. Fluorescent-labelled oligonucleotides that will allow quantitative PCR determination may be included (e.g. TaqMan chemistry, Molecular Beacons). Suitable enzymes for amplification of the DNA, will also be included.

Control nucleic acid may be included for purposes of comparison or validation. Such controls could either be RNA/DNA isolated from healthy tissue, or from healthy individuals, or housekeeping genes such as β-actin or GAPDH whose mRNA levels are not affected by virus infection. In additional embodiments, the kits may comprise instructions for use.

EXAMPLES

Example 1

Materials and Methods

Cells

Hela cells (ATCC CCL-2) were maintained in growth media (EMEM medium supplemented with 10% (v/v) foetal calf serum (FCS), 10 mM HEPES, 2 mM L-glutamine, 100 U/mL penicillin and 100 μg/mL streptomycin. African green monkey kidney epithelial Vero cells (ATCC CRL-81) were maintained in DMEM supplemented with 10% (v/v) FCS, 100 U/mL penicillin and 100 μg/mL streptomycin. All cells were incubated at 37° C. under a 5% $CO_2$/95% air atmosphere.

Infection of Hela Cells with Hendra Virus or Nipah Virus

Hela cells were seeded in 6 well plates ($5 \times 10^5$ cells/well) in growth medium. The following day, cells were infected with Hendra virus (Hendra virus/Australia/Horse/1994/Hendra) or Nipah virus at a multiplicity of infection (m.o.i.) of 2 for indicated time-points in triplicate.

Purification of Small RNAs from Hela Cells

Hela cells were lysed in 350 μL RLT buffer (Qiagen) and stored at −80° C. Small RNAs were purified using a protocol modified from the RNeasy Mini RNA Purification Kit protocol and the RNeasy MinElute Cleanup Kit protocol (Qiagen). Lysates were homogenised for 30 seconds using a rotor-stator homogenizer. One volume of 70% ethanol was added to homogenized lysates and mixed by pipetting. Samples were applied to an RNeasy spin column and centrifuged for 15 sec. at 8000×g. Eluent was retained, and added to 1.5 volumes of 100% ethanol. Samples were loaded onto an RNeasy MinElute Spin column, washed twice with RPE buffer and eluted in 50 μL of RNase-free water. Samples were treated with RNase-free DNase (Promega) according to manufacturer's instructions. Sample volume was adjusted to 100 μL with RNase-free water, and added to 350 μL RLT buffer. 700 μL of 100% ethanol was added to the diluted RNA, and mixed by pipetting. Samples were transferred to an RNeasy MinElute spin column and centrifuged for 15 seconds at 10,000 rpm. Columns were washed with RPE buffer and with 80% ethanol. RNA was eluted in 14 μL of RNase-free water.

miRNA Profiling

Expression levels of small RNAs from Hela cells were measured using a $RT^2$ miRNA PCR Array System (SA Biosciences—Qiagen) according to manufacturer's instructions. Firstly, small RNAs were converted to cDNA using a $RT^2$ miRNA First Strand Kit (SA Biosciences) according to manufacturer's instructions. Sample cDNA (100 ng) was combined with $RT^2$ qPCR Master Mix (SA Biosciences) according to manufacturer's instructions and applied to a $RT^2$ human miFinder miRNA PCR array (SA Biosciences). PCR arrays were run on an ABI Prism 7700 Sequence Detection System (Applied Biosystems). PCR cycling was performed as follows: 95° C. for 10 min., followed by 40 cycles of 95° C. for 15 sec., 60° C. for 30 sec. and 72° C. for 30 sec. Data was analysed using the $\Delta\Delta C_t$ method according to the PCR Array Data Analysis Web Portal (http://www.sabiosciences.com/perarraydataanalysis.php).

Ferret Hendra Virus Infections:

Male ferrets (aged 12-18 months) were infected with HeV as part of a trial described previously (Pallister et al., 2011).

Horse Hendra Virus Infections:

Three adult mares were infected with HeV as part of a trial described previously (Marsh et al, 2011).

Purification of RNA from Whole Blood:

Whole blood samples were collected in heparin on indicated days post-infection. Initial stages of RNA extraction were carried out at Biosafety Level-4 (BSL-4). RNA was purified using the RNeasy RNA purification kit (Qiagen) according to manufacturer's instructions. Briefly, samples (100 μL) were added to 262 μL MagMAX buffer and mixed thoroughly by vortexing. 180 μL of inactivated samples was added to 170 μL of RLT buffer (Qiagen), and incubated for 5 min. at room temperature. Two volumes of 70% ethanol were added and mixed well by pipetting. 700 μL of sample was transferred to an RNeasy spin column and centrifuged at 8000×g for 15 seconds. RNeasy tubes were washed with RW1 buffer (Qiagen) and twice with RPE buffer. RNA was eluted with 50 μL of nuclease-free water and stored at −80° C.

Preparation of Small RNA for Quantitative Real-Time PCR:

RNA samples from whole blood (~200 ng) were treated with RNase-free DNase (Promega) according to manufacturer's instructions. Polyadenylation of RNA samples was performed by incubating RNA (~200 ng) with 1U poly(A) polymerase (USB), 0.5 nM rATP (Ambion) in 1×poly(A) polymerase buffer (USB) at 37° C. for 30 min., then 95° C. for 5 min. cDNA synthesis was performed using Superscript III reverse transcriptase (Invitrogen) according to manufacturer's guidelines.

Quantitative Real-Time PCR:

Quantitative real-time PCR was performed on an ABI Prism 7700 Sequence Detection System. PCR cycling was performed as follows: 95° C. for 10 min., followed by 40 cycles of 95° C. for 15 sec., 60° C. for 1 min. Data was analysed using the $\Delta\Delta C_t$ method. Sequences of primers used for detection of miRNAs were:

```
PAM-URP                            (SEQ ID NO: 1)
5'-GAGGCGAGCACAGAATTAATACGAC-3';

mir-146a                           (SEQ ID NO: 2)
5'-GCGTGAGAACTGAATTCCATGGG-3';

5S                                 (SEQ ID NO: 3)
5'-TGGGAATACCGGGTGCTGT-3'.
```

Treatment of Hela Cells with Antagomirs and HeV Infection

Hela cells were seeded in 24 well plates ($4 \times 10^4$ cells/well) in growth media. The following day, cells were incubated with antagomirs specific to mir-146a ($a_s a_s$cccauggaauuca-guuc$_s$u$_s$c$_s$a$_s$-Chol; SEQ ID NO:4; s refers to phosphorothioate linkages) or a scramble negative control antagomir "antiscramble" (u$_s$a$_s$uuuacccuuuacuuguc$_s$u$_s$a$_s$u$_s$-Chol; SEQ ID NO:5). A C G U refer to 2' O Me A C G U, respectively. Final antagomir concentrations were 100 nM. 24 hours later, cells were infected with HeV (Hendra virus/Australia/Horse/1994/Hendra, m.o.i. 0.01). At 8 hours, 24 hours and 48 hours post-infection, 100 μL medium aliquots were taken for $TCID_{50}$ analysis and stored at −80° C.

$TCID_{50}$ Analysis:

10-fold dilutions of medium aliquots were made in PBS and added to a 96-well tissue culture plate containing Vero cells ($9 \times 10^3$ cells/well) in growth medium. Plates were incubated for 5 days at 37° C., 5% $CO_2$ and scored for cytopathic effect. The infectious titer was calculated by the method of Hawkes (1979).

Example 2 miRNA Profiling During HeV and NiV Infection In Vitro

The present inventors screened for miRNAs modulated by HeV and NiV infection. Nine miRNAs were identified that were differentially regulated by HeV in Hela cells (FIG. 1: mir-151-5p (SEQ ID NO:6); mir-146a (SEQ ID NO:7); mir-128 (SEQ ID NO:8); mir-140-3p (SEQ ID NO:9); mir-100 (SEQ ID NO:10); mir-28-3p (SEQ ID NO:11); mir-302c (SEQ ID NO:12); mir-150 (SEQ ID NO:13); mir-142-3p (SEQ ID NO:14)). Of particular interest was mir-146a; significantly up-regulated at 3 hours and ~20 fold-up-regulated after 8 hours HeV infection. Validation of the 8 hour timepoint result by quantitative PCR confirmed that the induction of 146a at 8 hours was statistically significant (not shown). FIG. 2 demonstrates that mir-146a is also upregulated during NiV infection.

Example 3

Levels of Mir-146a in a Ferret Model of HeV Infection

Ferrets act as a model for several viral respiratory diseases including HeV (Pallister et al., 2011). Levels of mir-146a were examined in whole blood collected from 4 ferrets during a HeV animal trial (FIG. 3). For ferret 1, levels of mir-146a increased ~15 fold compared to pre-infection levels at day 6 post-infection. Levels of HeV genome were first detected on day 6, and increased approximately 60-fold between day 6 and postmortem (day 8 for ferret 1). For ferret 2, maximum mir-146a levels were again detected on day 6 post-infection, with virus detected on day 3, but not increasing until the time between day 6 and post-mortem (day 9). For ferret 3, mir-146a was first detected day 3 post-infection, and increased between day 3 and day 6. HeV genome was first detected on day 6, and maximised on day 8. Postmortem for ferret 3 was day 9. For ferret 4, increases in mir-146a were detected between days 3 and 6, and again at post-mortem (day 8). One notable difference between ferret 4 and the other ferrets was the extent of mir-146a induction (~350 fold) compared to the other ferrets (5-20 fold).

Example 4

Levels of Mir-146a in a Horse Model of HeV Infection mir-146a levels were examined in blood taken from 3 horses infected with HeV as part of a BSL-4 animal trial (FIG. 4). For horse 1, a 3.5-fold increase in mir-146a was detected on day 1 post-infection. Maximum levels of mir-146a were detected on day 3 postinfection (~8-fold induction compared to pre-infection levels). HeV was first detected in the blood of horse 1 on day 4, and reached a maximum on day 8. For horse 2, increases in mir-146a were first observed day 1 post-infection, and maximised on day 3. HeV was first detected on day 5 post-infection, and maximised on day 7. For horse 3, an increase in blood mir-146a levels was detected on day 1 post-infection, and maximised on day 3. HeV was first detected on day 5 post-infection, and maximised on day 8.

Example 5

The Effect of Blocking Mir-146a on HeV Infection In Vitro

Having demonstrated the up-regulation of mir-146a during HeV infections both in vitro and in vivo, the present inventors tested the outcome of blocking mir-146a on HeV infection in vitro. The replication of HeV in Hela cells was measured over a 48 hour time course by $TCID_{50}$ assay (FIG. 5). HeV was added to cells that were either untreated, or treated for 24 hours with an inhibitor of mir-146a, or a scrambled negative control inhibitor (final concentration 100 nM). At 8 hours post-infection, cells treated with an inhibitor specific to mir-146a showed a significant decrease in virus titres ($2.80 \pm 5.4 \times 10^{-16}$ compared to $2.60 \pm 0.05$—a 36% reduction). At 24 hours post-infection, virus titres were again lower in cells treated with the mir-146a inhibitor ($4.30 \pm 0.50$) than untreated cells ($5.19 \pm 0.38$). This difference represented an 87% reduction that was statistically significant. At 48 hours post-infection, virus tires in untreated cells and cells treated for mir-146a inhibitor were not significantly different. At no stage during the HeV infection were virus titres in cells treated with the negative control inhibitor significantly different from untreated cells.

A second experiment was performed and involved $TCID_{50}$ measurement of Hendra virus titres in HeLa cell supernatants of cells treated with a miR-146a specific inhibitor or a negative control miRNA inhibitor. At multiplicity of infections (MOIs) of 0.01 and 0.1, Hendra virus replication was significantly reduced in cells treated with the miR-146a inhibitor, but not the negative control inhibitor (A) (FIG. 6). At a higher MOI of Hendra virus (MOI 1), there was no significant difference in virus titers between control cells and cells with blocked miR-146a. The miR-146a specific inhibitor also significantly reduced cellular virus levels from a 24 h infection with Hendra virus (MOI 0.1), as measured by QRT-PCR (B).

Example 6

Inhibition of NF-κB Suppresses Hendra Virus Replication

An alignment of mir-146a sequence with the human genome indicated that the target sequence of this miRNA molecule is RNF11. RNF11 is a member of the A20 ubiquitin-editing protein complex and modulates NF-κB signaling (Pranski et al., 2012). In vitro experiments in HeLa cells showed that the expression of RNF11 was reduced in cells transfected with mir-146a (data not shown). Further experiments demonstrated that mir-146a targeting of RNF11 promoted Hendra virus replication in vitro (data not shown).

As evidence suggests that RNF11 acts as a negative regulator of NF-κB, the present inventors tested the impact of blocking NF-κB activity on Hendra virus replication. HeLa cells were transfected with the IκB super-repressor gene, which sequesters NF-κB in an inactive conformation (DiDonato et al., 1995). Upon infection with Hendra virus, virus titers were significantly reduced in HeLa cells expressing the IκB superrepressor compared to control cells (FIG. 7; (A)). The inventors also measured Hendra virus replication in cells treated with two chemical compound inhibitors of NF-κB activity, Bay11-7082 (Pierce et al., 1997) and MG-132, which also inhibits the 26S proteosome (Lee and Goldberg, 1998). Hendra virus replication was significantly reduced by MG-132 and reduced (not significantly) by Bay11-7082 (B). At these concentrations, Bay11-7082 and MG-132 were not adversely impacting HeLa cell viability (C), suggesting that inhibition of Hendra virus replication by MG-132 was not due to toxicity. Collectively these results suggest that Hendra virus replication is favoured by NF-κB activity, and that NF-κB inhibitors can be used in the treatment or prevention of viral infection.

Example 7

Discussion

Results from this study can be viewed in the context of a recent animal trial characterising HeV infection in horses (Marsh et al, 2011). In this comprehensive trial, blood, urine, rectal swabs, nasal swabs, oral swabs and faeces were examined for the presence of HeV daily for the duration of the trial. Heart rate and body temperatures were also monitored in 12 hour intervals. For each of the 3 horses, HeV was detected earliest by quantitative real-time PCR of nasal swab samples, which indicated virus shedding 2 days post-infection. Quantitative real time PCR testing of blood, urine, rectal swabs, oral swabs and faeces remained negative for another 2-3 days, while increases in heart rate and body temperature were also observed several days later. A finding of major significance from the present study is that levels of mir-146a increased within 1 day of HeV infection in all 3 horses, thereby providing the earliest indication yet known of HeV infection.

The use of gene expression profiles to diagnose specific diseases has gained considerable interest, especially in cancer research (Liu et al., 2011; Kerr et al., 2011; Nana-Sinkam and Croce, 2011). Serum miRNA profiles have recently been used to develop a diagnostic tool that can differentiate between serum containing Hepatitis B virus or Hepatitis C virus (Li et al., year). The development of a miRNA-based diagnostic test for HeV and NiV infections could be invaluable, given (i) the high pathogenicity of HeV and NiV and associated risk of exposure and (ii) the fact that mir-146a induction in vivo occurs prior to other measures of infection. Furthermore, an increased level of miR-146a appears to be an early marker for ill-health and/or HeV or NiV infection in subjects where infection is suspected, thus helping in the early management of disease. A pertinent application of such information would be early recognition of contact infections (for example, in horses or humans) during the management of a HeV or NiV disease outbreak, allowing prompt instigation of control or therapeutic measures.

The impact of blocking mir-146a on HeV replication in vitro (FIGS. 5, 6 and 7) demonstrates that mir-146a plays a significant role in HeV pathogenesis. Validated target genes of mir-146a include IL-1 receptor-associated kinase 1 (IRAK1) and TNF receptor associated factor 6 (TRAF6) (Taganov et al., 2006), two adaptor molecules downstream of Toll-like and IL-1 receptors signalling pathways.

The results obtained by the present inventors also demonstrate that the modulation of NF-κB activity affects Hendra virus replication. Accordingly, NF-κB inhibitors can be used alone or in combination with miRNA antagonists in the treatment or prevention of viral infection.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

The present application claims priority from U.S. 61/533,978, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Baeuerle and Henkel (1994) Ann Rev Immunol, 12:141-179.
Baldwin (1996) Ann Rev Immunol 14:649-683.
Bartel (2009) Cell, 136: 215-233.
DiDonato et al. (1995) Mol Cell Biol, 15:1302-1311.
Driskell et al. (2009) Appl Spectrosc, 63:1107-1114.
Gardiner, D. J. (1989). Practical Raman spectroscopy. Springer-Verlag.
Hawkes (1979) In: Lennette EHaS, N.J., editor. *Diagnostic procedures for Viral, Rickettsial and Chlamydial infections*. Washington: American Public Health Association. pp. 3-48.
Kerr et al. (2011) Transl. Res, 157:241-252.
Kimmel (1987) Methods Enzymol, 152:507-511.
Lee and Goldberg (1998) Trends Cell Biol, 8:397-403.
Li et al. (2011) Cancer Res, 70:9798-9807.
Liu et al. (2011) Transl Res, 157:200-208.
Melotti et al. (2001) Gene Therapy 8:1436-1442.
Nana-Sinkam and Croce (2010) Cancer Genet. Cytogenet. 203:127-133.
Marsh et al. (2010) Emerg Infect Dis, 16:1767-1769.
Marsh et al. (2011) Emerg Infect Dis, 17:2232-2238.
Mitchell et al. (2008). Proc Natl Acad Sci USA, 105:10513-8.
Pallister et al. (2011) Vaccine, 29:5623-5630.
Pierce et al. (1997) J Biol Chem, 272:21096-21103.
Pranski et al. (2012) J Neuroinflammation, 9:67.
Song et al. (2010) Methods Mol Biol, 629:287-294.
Taganov et al. (2006) Proc Natl Acad Sci USA, 103:12481-12486.
Wahl and Berger (1987) Methods Enzymol, 152:399-407.
Wheeler et al. (2007) DNA Cell Biol, 26:251-255.

The invention claimed is:

1. A method for determining the likelihood of virus infection in a subject, the method comprising determining the level of at least one miRNA associated with virus infection in the subject, wherein an altered level of the at least one miRNA in the subject when compared to a control is indicative of an increased likelihood of virus infection, wherein the virus is a Henipavirus, and wherein the at least one miRNA includes an miRNA selected from miR-151-5p, miR-146a, miR-128, miR-140-3p, miR-100, miR-28-3p, miR-302c, miR-150 and/or miR142-3p.

2. The method of claim 1, wherein the Henipavirus virus is Hendra virus.

3. The method of claim 1, wherein the level of the at least one miRNA is increased when compared to the control.

4. The method of claim 1, wherein the at least one miRNA is selected from miR-146a, miR-150 and/or miR-142-3p.

5. The method of claim 1, wherein the at least one miRNA is miR-146a.

6. The method of claim 1, wherein the method comprises determining the level of the at least one miRNA in a blood sample obtained from the subject.

7. The method of claim 1, wherein the method comprises amplifying the miRNA.

8. The method of claim 7, wherein the miRNA is amplified by quantitative reverse transcription polymerase chain reaction.

9. The method of claim 1, wherein the subject is a human or a non-human animal.

10. The method of claim 1, wherein the method is performed before virus is detectable in a sample from the subject.

11. The method of claim 1, further comprising diagnosing virus infection in the subject.

12. A method of detecting virus replication in a biological sample obtained from a subject, the method comprising detecting in the sample a level of at least one miRNA associated with virus infection, wherein an altered level of the at least one miRNA in the sample when compared to a control is indicative of virus replication, wherein the virus is Henipavirus, and wherein the at least one miRNA is selected from miR-151-5p, miR-146a, miR-128, miR-140-3p, miR-100, miR-28-3p, miR-302c, miR-150 and/or miR142-3p.

13. A method for the early detection of a virus infection in a subject, the method comprising determining the level of at least one miRNA associated with virus infection in the subject, wherein an altered level of the at least one miRNA in the subject when compared to a control is indicative of a virus infection, wherein the virus is Henipavirus, and wherein the at least one miRNA includes an miRNA selected from miR-151-5p, miR-146a, miR-128, miR-140-3p, miR-100, miR-28-3p, miR-302c, miR-150 and/or miR142-3p.

14. The method of claim 13 which is performed during a suspected viral outbreak.

15. The method of claim 13, wherein the method detects the virus within five days of the subject having been infected.

16. The method of claim 13, wherein the method detects the virus within a day of the subject having been infected.

17. The method of claim 13 which is capable of detecting the viral infection before one or more of ELISA, PCR, immunofluorescence assay, serum neutralisation test and/or virus isolation.

18. The method of claim 13, wherein the Henipavirus is Hendra virus.

* * * * *

SEQUENCE LISTING

<160> NUMBER OF SEQ ID NOS: 14

<210> SEQ ID NO 1
<211> LENGTH: 25
<212> TYPE: DNA
<213> ORGANISM: artificial
<220> FEATURE:
<223> OTHER INFORMATION: PAM-URP oligonucleotide primer

<400> SEQUENCE: 1
gaggcgagca cagaattaat acgac 25

<210> SEQ ID NO 2
<211> LENGTH: 23
<212> TYPE: DNA
<213> ORGANISM: Artificial Sequence
<220> FEATURE:
<223> OTHER INFORMATION: mir-146a oligonucleotide primer

```
<400> SEQUENCE: 2
gcgtgagaac tgaattccat ggg                                          23

<210> SEQ ID NO 3
<211> LENGTH: 19
<212> TYPE: DNA
<213> ORGANISM: Artificial Sequence
<220> FEATURE:
<223> OTHER INFORMATION: 5S oligonucleotide primer

<400> SEQUENCE: 3
tgggaatacc gggtgctgt                                               19

<210> SEQ ID NO 4
<211> LENGTH: 22
<212> TYPE: RNA
<213> ORGANISM: Artificial Sequence
<220> FEATURE:
<223> OTHER INFORMATION: mir-146a antagomir

<400> SEQUENCE: 4
aacccaugga auucaguucu ca                                           22

<210> SEQ ID NO 5
<211> LENGTH: 22
<212> TYPE: RNA
<213> ORGANISM: Artificial Sequence
<220> FEATURE:
<223> OTHER INFORMATION: control antagomir

<400> SEQUENCE: 5
uauuuacccu uuacuugucu au                                           22

<210> SEQ ID NO 6
<211> LENGTH: 21
<212> TYPE: RNA
<213> ORGANISM: Artificial Sequence
<220> FEATURE:
<223> OTHER INFORMATION: mir-151-5p

<400> SEQUENCE: 6
ucgaggagcu cacagucuag u                                            21

<210> SEQ ID NO 7
<211> LENGTH: 22
<212> TYPE: RNA
<213> ORGANISM: Artificial Sequence
<220> FEATURE:
<223> OTHER INFORMATION: mir-146a

<400> SEQUENCE: 7
ugagaacuga auuccauggg uu                                           22

<210> SEQ ID NO 8
<211> LENGTH: 21
<212> TYPE: RNA
<213> ORGANISM: Artificial Sequence
<220> FEATURE:
<223> OTHER INFORMATION: mir-128

<400> SEQUENCE: 8
ucacagugaa ccggucucuu u                                            21

<210> SEQ ID NO 9
```

```
<211> LENGTH: 21
<212> TYPE: RNA
<213> ORGANISM: Artificial Sequence
<220> FEATURE:
<223> OTHER INFORMATION: mir-140-3p

<400> SEQUENCE: 9
uaccacaggg uagaaccacg g                                             21

<210> SEQ ID NO 10
<211> LENGTH: 22
<212> TYPE: RNA
<213> ORGANISM: Artificial Sequence
<220> FEATURE:
<223> OTHER INFORMATION: mir-100

<400> SEQUENCE: 10
aacccguaga uccgaacuug ug                                            22

<210> SEQ ID NO 11
<211> LENGTH: 22
<212> TYPE: RNA
<213> ORGANISM: Artificial Sequence
<220> FEATURE:
<223> OTHER INFORMATION: mir-28-3p

<400> SEQUENCE: 11
cacuagauug ugagcuccug ga                                            22

<210> SEQ ID NO 12
<211> LENGTH: 23
<212> TYPE: RNA
<213> ORGANISM: Artificial Sequence
<220> FEATURE:
<223> OTHER INFORMATION: mir-302c

<400> SEQUENCE: 12
uaagugcuuc cauguuucag ugg                                           23

<210> SEQ ID NO 13
<211> LENGTH: 22
<212> TYPE: RNA
<213> ORGANISM: Artificial Sequence
<220> FEATURE:
<223> OTHER INFORMATION: mir-150

<400> SEQUENCE: 13
ucucccaacc cuuguaccag ug                                            22

<210> SEQ ID NO 14
<211> LENGTH: 23
<212> TYPE: RNA
<213> ORGANISM: Artificial Sequence
<220> FEATURE:
<223> OTHER INFORMATION: mir-142-3p

<400> SEQUENCE: 14
uguaguguuu ccuacuuuau gga                                           23
```